United States Patent
Curran

[11] 3,984,430
[45] Oct. 5, 1976

[54] THIOHYDANTOIN DERIVATIVES

[75] Inventor: Adrian Charles Ward Curran, Newcastle-upon-Tyne, England

[73] Assignee: John Wyeth & Brother, Maidenhead, England

[22] Filed: Apr. 11, 1975

[21] Appl. No.: 567,446

[30] Foreign Application Priority Data
Apr. 19, 1974 United Kingdom............. 17219/74

[52] U.S. Cl............................. 260/309.5; 424/273
[51] Int. Cl.²......................................... C07D 49/32
[58] Field of Search................. 260/309.5; 424/273

[56] References Cited
UNITED STATES PATENTS 3,168,558 2/1965 Kurhajec et al. ............. 260/309.5 X
3,210,400 10/1965 Brakebill......................... 260/309.5

FOREIGN PATENTS OR APPLICATIONS 635,216 1/1962 Canada....................... 260/309.5 X

OTHER PUBLICATIONS

D. Elmore et al., Journ. Chem. Soc., 1956, pp. 192–196.

Primary Examiner—Ethel G. Love

[57] ABSTRACT

This invention relates to novel thiohydantoins having the formula:

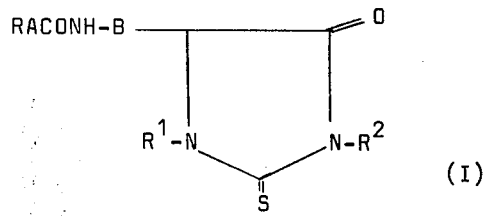

wherein R represents lower alkyl or a phenyl or phenyl lower alkyl radical in either of which the phenyl portion may be substituted by halogen, lower alkyl or lower alkoxy; A is oxygen or a direct bond; B represents lower alkylene, $R^1$ represents hydrogen, or lower alkyl; and $R^2$ represents lower alkyl or phenyl which may be substituted by halogen, lower alkyl or lower alkoxy, which possess anti-ulcer activity.

6 Claims, No Drawings

THIOHYDANTOIN DERIVATIVES

This invention relates to novel thiohydantoin derivatives possessing pharmacological activity, to processes for preparing them and to pharmaceutical compositions containing them.

More particularly this invention relates to novel thiohydantoins having the formula:

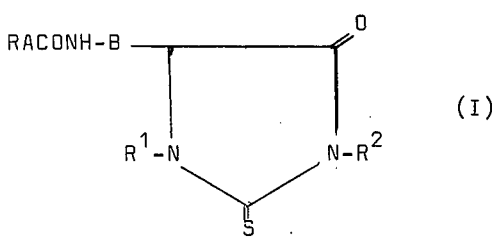

(I)

wherein R represents lower alkyl or a phenyl or phenyl lower alkyl radical in either of which the phenyl portion may be substituted by halogen, lower alkyl or lower alkoxy; A is oxygen or a direct bond; B represents lower alkylene; $R^1$ represents hydrogen, or lower alkyl; and $R^2$ represents lower alkyl or phenyl which may be substituted by halogen, lower alkyl or lower alkoxy.

By the term "lower" used in connection with the groups alkyl or alkylene is meant alkyl or alkylene group which contains from 1 to 6 carbon atoms and includes both straight and branched chains.

Examples of R are methyl, ethyl, n-propyl, isopropyl, t-butyl, phenyl or phenyl substituted by one or more groups which may be the same or different selected from halogen (for example fluorine, chlorine or bromine), lower alkyl (for example methyl, ethyl, propyl or butyl), lower alkoxy (for example methoxy, ethoxy, propoxy or butoxy). Other groups represented by R include benzyl, phenethyl, 3-phenylpropyl, all of which may be optionally substituted by one or more of the same groups mentioned above for phenyl. Preferably R is benzyl or benzyl substituted by halogen, for example p-chlorobenzyl, o-chlorobenzyl. Preferably A is oxygen. Examples of straight chain B radicals are methylene, ethylene, propylene and butylene; examples of branched chain B radicals are

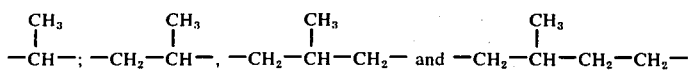

Preferably B is a straight chain of from 1 to 4 carbon atoms.

Examples of $R^1$ are hydrogen, methyl, ethyl, n-propyl, isopropyl or n-butyl. Preferably $R^1$ is hydrogen.

Examples of $R^2$ are methyl, ethyl and n-propyl, phenyl or phenyl substituted by the same groups as mentioned above in connection with the group R. Preferably $R^2$ is methyl.

It will be apparent to anyone skilled in the art that the compounds of formula (I) possess at least one asymmetric carbon atom and therefore optical isomers are possible. All such optical isomers or mixtures thereof are intended to be included within the scope of the present invention.

The compounds of formula (I) possess anti-ulcer activity for example as demonstrated by a standard procedure based on that by Brodie and Hanson, J. App. Physiol., 15: 291(1960).

The test procedure was:

Male rats, weighing between 80 and 120 gms., are fasted overnight with water ad lib. The rats are then divided into groups of six and dosed orally with the test drug, or with the vehicle alone, 0.5% carboxymethylcellulose, in a volume of 10 ml/kg. After 30 minutes the rats are inserted into aluminum restraining tubes measuring 1 5/8 inches in diameter by 5 inches and placed in the cold (4±1°C) for 3 hours. Immediately after cold exposure the rats are killed by intra-cranial alcohol injection and their stomachs excised and opened along the greater curvature. Each stomach is greatly rinsed free of contents with warm tap water and pinned out on a board. The condition of the gastric mucosa is then scored from 0 to 6 on the following scale:

| Ulcers 0 to 6 | | |
|---|---|---|
| 0 | = | No ulcers |
| 1 | = | Pin point haemorrhagic site |
| 2, 3 | = | Several discrete pin-point haemorrahagic sites |
| 4, 5, 6 | = | Large eroded sites with haemorrhage |

The maximum possible score for each animal was 6 and for the group 36.

Decrease in ulcer formation is calculated as a percentage of the control score, i.e.

$$\text{Percentage inhibition} = \frac{\text{Total control group score} - \text{Total test group score}}{\text{Total control group score}} \times 100$$

The statistical significance of the effect is assessed by Student's t-test.

For example, in the above test a representative compound of formula I, namely, 5-(4-benzyloxycarbonylaminobutyl)-3-methyl-2-thiohydantoin showed 83% activity at 100 mpk.

The compounds of formula I may also possess anti-inflammatory activity as demonstrated by the ability to inhibit experimentally-induced edema in the hind paw of rats according to the procedure of Winter et al., Proc. Soc. Exp. Biol. and Med., (1962), 111, 544 and Buttle et al., Nature (1957), 179, 629. The compounds are administered orally in a dose range of about 1 to about 100 mg/kg and the percentage inhibition of the swelling of the paw as compared to control animals is measured.

The present invention also includes processes for preparing the compounds of formula (I). One such process for preparing compounds of formula (I) comprises cyclising a compound of formula:

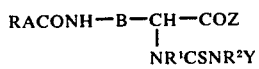
$$\text{RACONH—B—CH—COZ} \atop \text{NR}^1\text{CSNR}^2\text{Y}$$ (II)

wherein R,R¹,R², A and B are as defined above; Y is hydrogen or an acyl group, for example, a lower alkanoyl group, e.g. acetyl; and Z is hydroxy, $-O^-M^+$ wherein $M^+$ is an alkali metal cation, or halogen; or —COZ is an ester function, for example a lower alkyl ester, e.g. methyl ester (i.e. —COZ is —COOMe), or an amido function (i.e. —COZ is —CONH₂) and if necessary reacting any resulting free amine with a compound of formula:

RACOX (III)

wherein R is as defined above and X is halogen, e.g. chlorine, or an azide radical.

When Z is hydroxy or $-O^-M^+$ the cyclisation may be conveniently carried out in the presence of a solvent under acidic conditions, with heating if desired. When Y is hydrogen and —COZ is an ester or amide function or Z is a halogen then the cyclisation may be effected by heating or by allowing the compound of formula (II) to stand in solution, for example alcoholic ammonia solution, e.g. methanolic ammonia, for a period of time sufficient to permit cyclisation. When the cyclisation reaction is carried out under acidic conditions the RACO-moiety may be cleaved off during the reaction, for example when A is oxygen and R is lower alkyl, e.g. t-butyl, and therefore the free amine formed may be converted to compounds of formula (I) by reaction with a compound of formula (III) as defined above.

Compounds of formula (II) wherein Y is hydrogen and R² is other than hydrogen used in the above reaction may be prepared by reacting a compound of formula:

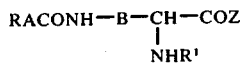
$$\text{RACONH—B—CH—COZ} \atop \text{NHR}^1$$ (IV)

wherein R,R¹,A B and Z are as defined above; with an isothiocyanate of formula R²—NCS, wherein R² is as defined above, at pH8–10 without heating.

Compounds of formula (II) wherein Y is an acyl radical, may be prepared by reacting a corresponding compound of formula (IV) with a compound of formula:

Y—NHCSSR³ (V)

wherein R³ is lower alkyl and Y is an acyl radical. The reaction may be carried out in slightly basic media, e.g. pH about 9.

When a compound of formula (IV) wherein —COZ is an ester or amide function, is reacted with a compound of formula R²—NCS in substantially neutral solution with heating, then it is possible to obtain a corresponding compound of formula (I) directly.

A futher process for the preparation of compounds of formula (I) comprises reacting a compound of formula:

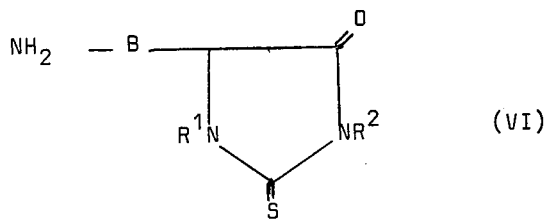

(VI)

wherein R¹, R² and B are as hereinbefore defined, with a compound of formula:

RACOX (III)

wherein R, A and X are as hereinbefore defined. When X is halogen the reaction may conveniently be carried out in the presence of base, for example an alkali metal hydroxide or bicarbonate. When X is an azide radical the reaction may be carried out under mildly acidic conditions.

Some of the compounds of formula (VI) are known compounds and reference may be made to the literature for methods of preparing them. The novel compound of formula (VI) may be prepared by analogous processes.

The invention also includes pharmaceutical compositions comprising a compound of formula (I) together with a pharmaceutical carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without carriers) is surrounded by carrier, which is thus in association with it. Similarly cachets are included.

Sterile liquid compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent; for instance aqueous propylene glycol containing from 10 to 75% of the glycol by weight is generally suitable. In other instances compositions can be made by dispersing the finely-divided active ingredient in aqueous starch or sodium carboxymethyl cellulose, or in a suitable oil, for instance arachis oil.

Preferably the pharmaceutical composition is in unit dosage form, in which form the composition is subdivided in unit doses containing appropriate quantities of the active ingredient. The unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The anti-ulcer composition of the invention will be administered orally in either liquid or solid composition form. These compositions may include one or more antacid ingredients, e.g. aluminium hydroxide, magnesium hydroxide, bismuth carbonate, aluminium glycinate, calcium carbonate, magnesium trisilicate, sodium bicarbonate or the alumina gel described in U. K. patent specification No. 1,284,394.

The following Examples illustrate the invention:

EXAMPLE 1

5-(4-Benzyloxycarbonylaminobutyl)-3-methyl-2-thiohydantoin

A solution of $N^\epsilon$-benzyloxycarbonyl-L-lysine methyl ester (4.66 g., 0.016 mol.) (prepared from L-lysine according to the method of Bergmann et al., J. Biol. Chem. 1935, 111, 245) in acetonitrile (20 ml.) was treated with methyl isothiocyanate (1.16 g., 0.016 mol.) and the mixture heated at reflux for 3 hours. The solvent was removed in vacuo and the residual oil triturated with ethanol to give a white solid which recrystallised from ethanol to give the title compound as colourless needles (1.2 g.) m.p. 135°C. (Found: C, 57.3; H, 6.4; N, 12.2; $C_{16}H_{21}N_3O_3S$ requires: C, 57.3; H, 6.3; N, 12.5%).

EXAMPLE 2

5-(4-Benzyloxycarbonylaminobutyl)-3-methyl-2-thiohydantoin

The mother liquor remaining from the recrystallisation of Example 1 was evaporated in vacuo and the residual oil (3.6 g.), believed to contain $N^\epsilon$-benzyloxycarbonyl-$N^\alpha$-(N-methylthiocarboxamido)-L-lysine methyl ester was dissolved in methanol previously saturated with ammonia, and allowed to stand at ambient temperature in a sealed flask for 3 days. The solvent was removed in vacuo and the residue recrystallised from ethanol to give the title compound as colourless needles (2.0 g.) m.p. 135°C.

EXAMPLE 3

5-(4-Benzamidobutyl)-3-methyl-2-thiohydantoin

A solution of $N^\epsilon$-benzoyl-L-lysine methyl ester (26 g) and methyl isothiocyanate (6.75 g) in ethanol (250) was heated under reflux for 12 hours. The solution was saturated with ammonia at 0°C and heated in a bomb at 40°C for 3 days. Evaporation of the solvent gave a gum which was crystallised from isopropyl alcohol. Recrystallisation from iso-propyl alcohol gave the title compound as the quarter isopropyl alcohol solvate 10 g (m.p. 137–8°C). Found: C, 59.4; H, 6.25; N, 13.1. $C_{15}H_{19}N_3O_2S.\frac{1}{4}C_3H_8O$ requires C, 59.0; H, 6.6; N, 13.1%.

EXAMPLE 4

5-(4-tert-Butyloxycarbonylaminobutyl)-3-methyl-2-thiohydantoin

Using an analogous procedure to Example 1 $N^\epsilon$-t-butyloxycarbonyl-L-lysine methyl ester may be reacted with methyl isothiocyanate to give the title compound.

EXAMPLE 5

5-(4-[p-Chlorobenzyloxycarbonylamino]butyl)-3-methyl-2-thiohydantoin

Using an analogous procedure to Example 1 $N^\epsilon$-p-chlorobenzyloxycarbonyl-L-lysine methyl ester may be reacted with methyl isothiocyanate to give the title compound.

EXAMPLE 6

5-(3-Benzyloxycarbonylaminopropyl)-3-methyl-2-thiohydantoin

Using an analogous procedure to Example 1 $N^\delta$-benzyloxycarbonyl-L-ornithine methyl ester may be reacted with methyl isothiocyanate to give the title compound

EXAMPLE 7

5-(4-Benzyloxycarbonylaminobutyl)-3-phenyl-2-thiohydantoin

Using an analogous procedure to Example 1 $N^\epsilon$-benzyloxycarbonyl-L-lysine methyl ester may be reacted with phenyl isothiocynate to give the title compound.

EXAMPLE 8

5-(4-Acetamidobutyl)-3-methyl-2-thiohydantoin

Using an analogous procedure to Example 1 $N^\epsilon$-acetyl-L-lysine methyl ester may be reacted with methyl isothiocyanate to give the title compound.

EXAMPLE 9

5-(3-Acetamidopropyl)-3-methyl-2-thiohydantoin

Using an analogous procedure to Example 1 $N^\delta$-acetyl-L-ornithine methyl ester may be reacted with methyl isothiocyanate to give the title compound.

EXAMPLE 10

5-(4-p-Methylbenzyloxycarbonylaminobutyl)-3-methyl-2-thiohydantoin

Using an analogous procedure to Example 1 N$^\epsilon$ -p-methylbenzyloxycarbonyl-L-lysine methyl ester may be reacted with methyl isothiocyanate to give the title compound.

EXAMPLE 11

5-(4-p-Methoxybenzyloxycarbonylaminobutyl)-3-methyl-2-thiohydantion

Using an analogous procedure to Example 1 N$^\epsilon$ -p-methoxybenzyloxycarbonyl-L-lysine methyl ester may be reacted with methyl isothiocyanate to give the title compound.

EXAMPLE 12

5-(4-p-Chlorobenzamidobutyl)-3-methyl-2-thiohydantoin

Using a procedure analogous to Example 1 N$^\epsilon$ -p-chlorobenzoyl-L-lysine methyl ester may be reacted with methylisothiocyante to give the title compound.

EXAMPLE 13

5-(4-Benzyloxycarbonylaminobutyl)-1,3-dimethyl-2-thiohydantoin

Using an analogous procedure to Example 1 N$^\epsilon$ -benzyloxycarbonyl-N$^\alpha$ -methyl-L-lysine methyl ester may be reacted with methyl isothiocyanate to give the title compound.

I claim:

1. A compound having the formula:

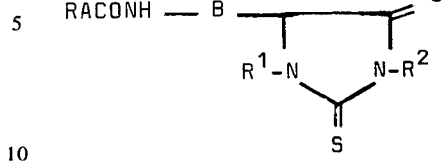

(I)

wherein R represents lower alkyl or a phenyl or phenyl lower alkyl radical, in either of which the phenyl portion may be substituted by halogen, lower alkyl or lower alkoxy; A is oxygen; B represents lower alkylene; R$^1$ represents hydrogen or lower alkyl; and R$^2$ represents lower alkyl or phenyl which may be substituted by halogen, lower alkyl or lower alkoxy.

2. A compound according to claim 1 wherein R is benzyl, halobenzyl, lower alkylbenzyl or lower alkoxybenzyl and A is oxygen.

3. A compound according to claim 1 wherein R$^2$ is methyl or phenyl.

4. A compound according to claim 1 wherein R$^1$ is hydrogen.

5. A compound according to claim 1 wherein R represents benzyl, halobenzyl, lower alkylbenzyl, lower alkoxybenzyl; A represents oxygen, R$^1$ represents hydrogen, R$^2$ represents methyl, and B represents lower alkylene of 1 to 4 carbon atoms.

6. A compound according to claim 1 which is 5-(4-benzyloxycarbonylaminobutyl)-3-methyl-2-thiohydantoin.

* * * * *